United States Patent [19]
Biere et al.

[11] Patent Number: 5,179,111
[45] Date of Patent: Jan. 12, 1993

[54] IMIDAZOLE DERIVATIVES

[75] Inventors: Helmut Biere; Ralph Rohde; Herbert H. Schneider; Lechoslaw Turski, all of Berlin, Fed. Rep. of Germany

[73] Assignee: Schering Aktiengesellschaft, Berlin, Fed. Rep. of Germany

[21] Appl. No.: 284,223

[22] Filed: Dec. 14, 1988

[30] Foreign Application Priority Data

Dec. 14, 1987 [DE] Fed. Rep. of Germany ....... 3742716

[51] Int. Cl.$^5$ ............... C07D 233/40; C07D 413/04; A01K 39/415
[52] U.S. Cl. .................... 514/341; 514/364; 514/397; 514/400; 546/227; 548/131; 548/333.5; 548/334.5; 548/337.1; 548/315.4; 548/311.1; 548/315.1; 548/314.7; 548/312.7; 548/311; 548/311.4
[58] Field of Search ............ 548/131, 343, 336; 546/277; 514/341, 364, 397, 400

[56] References Cited

U.S. PATENT DOCUMENTS 4,780,539 10/1988 Watjen .................... 598/131
4,952,698 8/1990 Biere et al. ................ 548/131

FOREIGN PATENT DOCUMENTS 1268 7/1987 World Int. Prop. O. .......... 548/131

OTHER PUBLICATIONS

Ktritzky, Comprehensive Heterocyclic Chemistry vol. 5, p. 468 (1952).

*Primary Examiner*—Robert Gerstl
*Attorney, Agent, or Firm*—Millen, White, Zelano and Branigan

[57] ABSTRACT

Imidazole derivatives of general Formula I

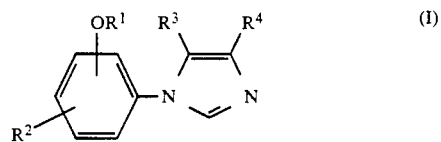

wherein $R^1$ means hydrogen, an optionally substituted $C_{1-10}$ hydrocarbon or hetaryl residue, or a cyclic ether residue, $R^2$ means hydrogen, halogen, an optionally substituted amino, nitro, azide, thiocyanate or cyano group, a linear or branched $C_{1-10}$-alkyl residue optionally substituted with halogen, or $-OR^1$ wherein $R^1$ has the above-mentioned meanings, and $R^1$ and $R^2$ jointly with the oxygen atom form a saturated or unsaturated 5- to 7-membered ring which can contain still another hetero atom, $R^3$ means hydrogen, a linear or branched $C_{1-6}$-alkyl group, or a $C_{1-6}$-alkoxyalkyl group, $R^4$ means $-COOR^5$, $-CONR^6R^7$, $-CN$,

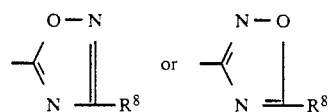

and their use as medicinal agents are disclosed.

13 Claims, No Drawings

IMIDAZOLE DERIVATIVES

SUMMARY OF THE INVENTION

The invention relates to novel CN-active imidazole derivatives of general Formula I

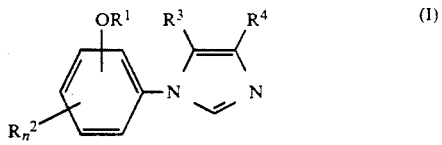

wherein
$R^1$ means hydrogen, an optionally substituted $C_{1-10}$ hydrocarbon or heteroaryl residue, or a cyclic ether residue,
$R^2$ means hydrogen, halogen, an optionally substituted amino, nitro, azide, thiocyanate or cyano group, a linear or branched $C_{1-10}$-alkyl residue optionally substituted with halogen, or —$OR^1$ wherein $R^1$ has the above-mentioned meanings, or
$R^1$ and $R^2$ jointly with the oxygen atom form a saturated or unsaturated 5- to 7-membered ring which can contain still another hetero atom,
n is 1 or 2,
$R^3$ means hydrogen, a linear or branched $C_{1-6}$ alkyl group, or a $C_{1-6}$-alkoxyalkyl group,
$R^4$ means —$COOR^5$, —$CONR^6R^7$, or —CN,

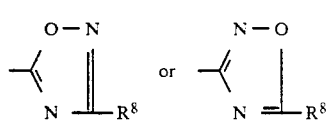

$R^5$ meaning hydrogen, a linear or branched $C_{1-6}$-alkyl group, $R^6$ and $R^7$ being identical or different and representing hydrogen or a linear, branched or cyclic alkyl group of up to 7 carbon atoms, or jointly with the nitrogen atom forming a saturated five- or six-membered ring that optionally contains a further hetero atom, $R^8$ meaning hydrogen or a linear, branched or cyclic alkyl group of up to 7 carbon atoms,
wherein $R^2$ can be present singly or severally at the phenyl residue.

DETAILED DISCUSSION

The substituents on the phenyl residue can be in the o-, m- or p-position; the residue $R^2$ can, in particular, occur once to twice, and the residues $R^2$ and —$OR^1$ can be identical or different. Halogen is understood to mean in each case fluorine, chlorine, bromine or iodine.

Suitable as the hydrocarbon residue $R^1$ are saturated or unsaturated, straight-chain or branched, optionally substituted alkyl groups of preferably 1-6 carbon atoms, furthermore saturated or unsaturated cycloalkyl or cycloalkylalkyl groups of preferably 3-7 carbon atoms, wherein a $CH_2$ group can optionally be replaced by an oxygen atom, as well as optionally substituted aryl or aralkyl groups of maximally 10 carbon atoms.

Saturated, straight-chain or branched alkyl residues are preferably in each case the lower alkyl residues, such as methyl, ethyl, propyl, isopropyl, butyl, sec-butyl, isobutyl, tert-butyl, as well as pentyl, hexyl, 2-methylbutyl, 2,2-dimethylpropyl.

The following alkenyl and alkynyl residues can be cited as preferred unsaturated alkyl groups: 1-propenyl, 2-propenyl, 3-methyl-2-propenyl, 2-propynyl.

Suitable substituents for the alkyl groups are halogens, such as, in particular, fluorine, chlorine and bromine, hydroxy, $C_{1-4}$-alkoxy and amino groups which can optionally also be mono- or disubstituted by lower alkyl groups (e.g., $C_{1-4}$). If the substituent is fluorine, then the perfluoroalkyl compound is to be considered preferred. For the remaining substituents, 1-2 substitutions are preferred.

Cycloalkyl residues are understood to mean in each case saturated residues, such as, for example, cyclopropyl, cyclobutyl, cyclopentyl, cyclohexyl, cycloheptyl, as well as unsaturated residues, such as, for example, cyclopentenyl.

If the hydrocarbon residue means a cycloalkylalkyl group, the cyclopropylmethyl, cyclopropylethyl and cyclopentylmethyl groups are considered preferred.

Suitable cycloalkyl groups interrupted by an oxygen atom are, for example, the cyclic ether groups 3-tetrahydrofuranyl and 3-tetrahydropyranyl. If the hydrocarbon residue means an aryl or aralkyl group, this group can be mono- to trisubstituted, e.g. with halogen, nitro, cyano, hydroxy, mercapto, $C_{1-4}$-alkyl, $C_{1-4}$-alkoxy, $C_{1-4}$-alkylthio, $C_{1-4}$-alkylsulfinyl, $C_{1-4}$-alkylsulfonyl, or an amino group mono- or disubstituted with $C_{1-4}$-alkyl, acyl e.g. $C_{1-4}$-alkanoyl) or sulfonyl. Preferred cyclic ethers have 5–6-membered rings.

Substituted phenyl can be cited as a preferred aryl residue, which can optionally be mono- or disubstituted with halogen or a cyano, nitro or optionally substituted amino group, such as, for example, 2,4-dichlorophenyl, 2-cyanophenyl, 4-aminophenyl, and others.

The aralkyl residue $R^1$ can be linear or branched in the alkyl residue and can optionally be mono- or disubstituted in the aryl residue, preferably with halogen, $C_{1-4}$-alkoxy, $C_{1-4}$-alkyl or with optionally substituted amino, e.g., by $C_{1-4}$-alkyl, acyl or sulfonyl: as above.

Ar-$C_{1-2}$-alkyl radicals are preferred which can be substituted in the aryl residue by 1-2 halogen atoms, especially bromine and chlorine, such as, for example, benzyl, phenethyl, α-methylbenzyl, 4-chlorophenethyl, 3-bromobenzyl, etc.

In case $R^1$ means a heteroaromatic residue, the latter can be 5- or 6-membered and can contain one to two hetero atoms, such as sulfur, nitrogen and/or oxygen and can optionally be substituted with the substituents recited for the aryl residue.

Six-ring heteroaromatics are preferred that have one to two nitrogen atoms and five-ring heteroaromatics with one to two oxygen, sulfur and/or nitrogen atoms which can be substituted by halogen, such as, for example, pyridine, pyrimidine, pyrazine, pyridazine, furan, thiophene, pyrrole, imidazole, thiazole. In particular, preferred residues that can be mentioned are pyridine, pyrimidine, pyrazine, thiazole and 5-bromopyridine.

In case $R^1$ and $R^2$ are adjacent, they may form a ring jointly with the oxygen atom, the hydrocarbon bridge can contain 1-3 carbon atoms, such as, for example, methylene, ethylene, ethylidene, propylene, and furthermore still another hetero atom, preferably oxygen.

If $R^6$, $R^7$ form jointly with the nitrogen atom a saturated heterocyclic five- or six-membered ring which can optionally contain a further hetero atom, this ring represents, for example, pyrrolidine, piperidine, morpholine, piperazine or thiomorpholine and can optionally be substituted with one to two $C_{1-4}$-alkyl groups, such as, for example, 2,6-dimethylmorpholine or N-methylpiperazine.

Where $R^2$ is $OR^1$, $R^1$ may be any moiety defined for $R^1$ above.

A preferred residue $R^3$ in its meaning of alkoxyalkyl is considered to be $C_{1-4}$-alkoxy-$C_{1-4}$-alkyl, especially $C_{1-4}$-alkoxymethyl.

The imidazole derivatives which are substituted in accordance with this invention surprisingly show an affinity to the benzodiazepine receptors although they differ greatly from the benzodiazepines in their chemical structure, and at the same time exhibit only low toxicity. Benzodiazepines show, for example, anticonvulsive, anxiolytic and muscle-relaxing, as well as sedative effects. Thus, the compounds of the invention can exert, for example, on the properties known from benzodiazepines, agonistic, inverse-agonistic, and antagonistic effects.

The compounds of this invention are suited, based on their biological efficacy, as psychopharmaceuticals, especially anxiolytics, e.g., for administration to mammals, including for human medicine. They can be formulated into psychopharmaceutical preparations, e.g., for oral and parenteral use.

Suitable formulating aids are physiologically compatible organic and inorganic excipients inert with respect to the compounds according to the invention.

Examples for excipients are water, saline solutions, alcohols, polyethylene glycols, polyhydroxyethoxylated castor oil, gelatin, lactose, amylose, magnesium stearate, talc, silicic acid, fatty acid mono- and diglycerides, pentaerythritol fatty acid esters, hydroxymethylcellulose and polyvinylpyrrolidone.

The pharmaceutical preparations can be sterilized and/or combined with auxiliary agents, such as lubricants, preservatives, stabilizers, wetting agents, emulsifiers, buffers, and colorants.

Especially suitable for parenteral use are injection solutions or suspension, especially aqueous solutions of the active compounds in polyhydroxyethoxylated castor oil. Usable carrier systems are also auxiliary surfactants, such as salts of the bile acids or animal or vegetable phospholipids, but also mixtures thereof, as well as liposomes or their components.

Particularly suited for oral administration are tablets, dragees or capsules with talc and/or a hydrocarbon carrier or binder, e.g. lactose, cornstarch or potato starch. Use can also take place in liquid form, such as, for example, as an elixir to which a sweetener has been added, if desired.

The compounds of this invention are applied in a dosage unit of 0.05–10 mg of active compound in a physiologically compatible carrier.

The compounds of this invention are utilized in a dose of 0.1–300 mg/day, preferably 1–30 mg/day, e.g., for administration to adult humans. The compounds of this invention can be used as anxiolytics, analogously to Diazepam, to treat, e.g., anxiety.

The compounds of this invention according to general Formula I are prepared by the process that (a) an aniline of general Formula II

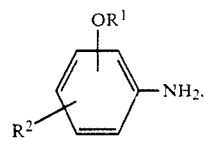

wherein $R^1$ and $R^2$ have the meanings given in Formula I, is reacted with a 2-azadiene of general Formula III

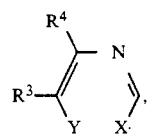

wherein $R^3$ and $R^4$ have the meanings given in Formula I and X and Y are fugitive groups, in the presence of acids at temperatures of 0° to 150° C.;

(b) an imidazole derivative of general Formula IV

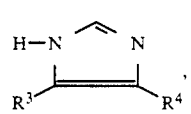

wherein $R^3$ and $R^4$ have the meanings given above, is arylated with an aromatic of general Formula V

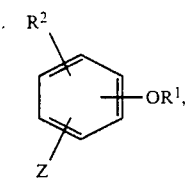

wherein $R^1$ and $R^2$ have the meanings set forth above and Z is a fugitive group, and optionally subsequently, an ester group present in the molecule is interesterified or saponified, a free carboxy group, optionally esterified, is amidated or reacted with an amidoxime of the formula $R^8-C(=NOH)NH_2$ to the 5-oxadiazolyl derivative and, if desired, a nitrile group present in the molecule is hydrolyzed to the carbonylamide or carboxy group or converted via the imino ester group into the ester group ($COOR^5$) or with hydroxylamine via the amidoxime and subsequently with an alkanecarboxylic acid of the formula $R^8-COOH$ or an activated derivative of the acid into the 3-oxadiazolyl derivative, and optionally compounds wherein $R^1=H$ are etherified in the presence of bases with the optionally substituted $C_{1-10}$ hydrocarbon or hetaryl residue, and optionally a nitro group is reduced to the amino group and the latter is then optionally alkylated or acylated or exchanged against halogen, azide, cyano or thiocyanate.

The reaction of anilines of Formula II according to this invention with 2-azadienes of Formula III to the imidazole derivatives of Formula I takes place in the presence of acids at temperatures of 0°–150° C. The fugitive groups X and Y can be identical or different; especially suited are $C_{1-3}$-dialkylamines, such as dimethyl-, diethyl- and dipropylamine, and cyclic amines, such as pyrrolidine.

The reaction is executed, for example, by first agitating the aniline derivative and the azadiene in an organic acid, such as, for example, formic acid, acetic acid, propionic acid or trifluoroacetic acid, at room temperature and then heating the reaction mixture up to its boiling temperature (up to about 120° C.).

The acid can simultaneously serve as the reactant and also as the solvent. However, it is also possible to add solvents, such as, for example, alcohols, ethers, ketones, esters, such as ethyl acetate, hydrocarbons, such as toluene, or halogenated hydrocarbons, such as carbon tetrachloride.

The amount of the acid can be varied within wide limits, but the acid is used in excess. Preferably, a 3- to 10-fold excess of the acid, based on the aniline and the azadiene, is selected.

The molar ratios of aniline and azadiene are uncritical for the success of the reaction. In general, approximately equal molar amounts of the reactants will be utilized, quantitative ratios of 1 mole of aniline and 1-3 moles of azadiene being preferred. The reaction according to this invention can basically also be conducted in the above-mentioned solvents with catalytic amounts of mineral acids, such as sulfuric acid, hydrochloric acid, perchloric acid or organic acids, such as p-toluenesulfonic acid and trifluoroacetic acid.

The advantage of the process according to this invention, following method (a), resides in the chemoselective synthesis of imidazole derivatives with the formation of only one isomer in a single process stage.

The N-arylation of the imidazole derivatives of general Formula IV can take place, for example, according to the method described by N. W. Gilman et al., J. Heterocycl. Chem. 14: 1157 (1977). In this procedure, it is necessary for the aromatic of general Formula V to be substituted with at least one electron-withdrawing group and with a fugitive group. Especially suitable as the electron-withdrawing groups are NO₂ and CN, and as the fugitive group Z halogens, especially fluorine and iodine can be employed. The arylation according to method (b) is performed in the presence of bases, such as alkali hydroxide, alkali hydride, optionally in the presence of phase transfer catalysts, butyllithium or lithium diisopropylamide, preferably with alkali hydride.

Suitable temperatures for, the reaction are −78° C. to 100° C., preferably 0° C. to 50° C.

Aprotic polar solvents can be utilized as solvents for the arylation, e.g. aliphatic and cyclic ethers, such as diethyl ether, tetrahydrofuran, etc., and dimethylformamide.

All conventional methods are suited for the optionally subsequently conducted interesterification. An example that can be cited is the reaction of the carboxylic acid ester with the corresponding alcohol in the presence of the alcoholate or with the corresponding alcohol with titanium tetraalcoholate or with the alcohol in the presence of an acid. The interesterification is performed at temperatures of about 0° to 120° C.

The optionally subsequently following saponification of the ester group takes place suitably under alkaline conditions, the ester being heated in dilute aqueous or alcoholic alkali solution, such as potassium or sodium hydroxide, up to the reflux temperature.

Esterification of the carboxy group takes place conventionally with the corresponding alcohol in an acid or in the presence of an activated acid derivative. Examples of suitable activated acid derivatives are acid chloride, acid imidazolide or acid anhydride.

For amidation, the imidazole-4-carboxylic acid or the corresponding ester is reacted with the aid of N,N'-carbonyldiimidazole or dicyclohexylcarbodiimide with a primary or secondary amine of the general formula

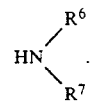

The reaction can also be conducted in a manner known per se by way of activated acid derivatives, such as via the anhydride or the mixed anhydride with chloroformic acid ester. Customarily, the amidation will be performed in an aprotic solvent, such as dimethylformamide, tetrahydrofuran, toluene or methylene chloride at temperatures of about 0° to 100° C.

For the introduction of the 5-oxadiazolyl residue, it is also possible to condense the imidazole-4-carboxylic acid with an amidoxime of the formula $R^8$—C(=NOH)NH₂ wherein $R^8$ has the meanings indicated in Formula I, in an inert solvent at room temperature up to the boiling temperature of the reaction mixture. Examples of suitable inert solvents are toluene and dimethylformamide. The free carboxylic acid is suitably activated in a fitting way prior to the condensation reaction. For this purpose, the free acid can be converted into the mixed anhydride, into the activated ester or into the chloride. An activation with imidazole/thionyl chloride in an aprotic solvent, such as dioxane, tetrahydrofuran, dimethylformamide or N-methylpyrrolidone at temperatures of between 0° and 50° C. has worked well.

The optionally following modification of the nitrile group can be conducted according to known methods. For example, the nitrile group can be converted by acidic or alkane hydrolysis into the carbonylamide or carboxy group or with the corresponding alcohol, with addition of gaseous hydrogen chloride, via the imino ester group into the ester group.

For the introduction of the 3-oxadiazolyl residue, the imidazole-4-carbonitrile is conventionally reacted to the amidoxime with hydroxylamine and then condensed in an inert solvent with an alkanecarboxylic acid of the formula $R^8$—COOH wherein $R^8$ has the meanings given in Formula I, or with an activated derivative of the acid. The condensation is performed in the same way as in case of the 5-oxadiazolyl compound.

Etherification of compounds of general Formula I with $R^1$=H takes place according to methods known per se. For example, a reactive derivative $R^1X$ can be reacted in a polar solvent in the presence of a base at temperatures of room temperature to the boiling temperature of the solvent, optionally also in the presence of a phase transfer catalyst. Especially suitable as the reactive residue X is a halogen, such as chlorine, bromine or iodine, as well as the mesyl or tosyl group. Bases that can be used are alkali compounds, such as sodium or potassium hydroxide, sodium or potassium carbonate, and others.

The reduction of the nitro group to the amino group can take place, for example, catalytically by hydrogenation reaction under normal pressure or H₂ pressure in polar solvents at room temperature. As the catalyst, palladium on a support, such as carbon, or platinum in finely divided form can be utilized; in case of compounds with halogen, the preferred catalyst utilized is Raney nickel. Polar solvents suitable for the reduction are, for example, alcohols or ethers, such as methanol, ethanol, diethyl ether, tetrahydrofuran or mixtures thereof.

The introduction of the cyano group can take place with the aid of the Sandmeyer reaction; for example, the diazonium salts intermediarily formed from the amino compounds with nitrites can be reacted with alkali cyanides in the presence of Cu(I) cyanide.

Introduction of the halogens chlorine, bromine or iodine by way of the amino group can also take place, for example, according to Sandmeyer by reacting the diazonium salts formed intermediarily with Cu(I) chloride or Cu(I) bromide in the presence of the corresponding acid, hydrochloric acid or hydrobromic acid, or by reaction with potassium iodide.

The introduction of fluorine is accomplished, for example, by Balz-Schiemann reaction of the diazonium tetrafluoroborate.

Introduction of the azido or thiocyanate group can likewise take place by way of Sandmeyer reaction of the diazonium salt with alkali azide or alkali thiocyanate.

If an alkylation or acylation of the amino group is desired, then the alkylation or acylation can be performed according to usual methods, for example, with alkyl halogenides or acyl halogenides.

The anilines of general Formula II and azadienes of general Formula III used as starting compounds are known in the majority or can be produced according to methods known per se.

For example, 2-azadienes have been described in Liebigs Ann. Chem. 1980: 344 and in DOS 2,919,891 and in Liebigs Ann. Chem. 1986: 1749.

The 2-azadienes utilized in the examples are prepared as disclosed in the examples set forth below:

Azadiene 1

1,4-Bis(dimethylamino)-2-aza-1,3-butadiene-3-carboxylic Acid Ethyl Ester

This compound is synthesized in accordance with Liebigs Ann. Chem. 1980: 344.

Azadiene 2

1,4-Bis(dimethylamino)-3-(3-ethyl-1,2,4-oxadiazol-5-yl)-2-aza-1,3-butadiene

This compound is synthesized in accordance with Liebigs Ann. Chem. 1986: 1749.

Azadiene 3

1,4-Bis(dimethylamino)-3-cyano-2-azabutadiene

A mixture of 45 g of aminoacetonitrile and 190 g of dimethylformamide dimethylacetal is heated under exclusion of moisture for 6 hours at 150° C. (bath temperature). During this step, about 130 ml of readily volatile material (methanol) is distilled off. After fractional distillation under vacuum, 125.6 g (75.6%) of azadiene is obtained with a boiling point of 115°-125° C. (0.03 torr), melting point 78°-81° C. (n-hexane).

Azadiene 4

(a) Dimethylaminomethyleneacetonitrile

By performing the step described in the preparation directions for azadiene 3 at a lower temperature (bath temperature 100° C.), then 79.2 g (89%) of dimethylaminomethyleneacetonitrile is obtained with a boiling point of 64°-67° C. (0.1 torr).

(b)

3-Cyano-1-dimethylamino-4-pyrrolidino-2-aza-1,3-pentadiene (E,Z Mixture)

A mixture of 22 g of dimethylaminomethyleneacetonitrile, 27 g of dimethylacetamide dimethylacetal, and 14 g of pyrrolidine is heated for 48 hours to 80° C. (bath temperature). After concentration under vacuum and subsequent bulb tube distillation, 30 g of azadiene is obtained with a boiling point of 160°-185° C. (0.08 torr). Subsequent crystallization from n-hexane yields crystals having a melting point of 49°-53° C.

Azadiene 5

(a)

3-Ethyl-5-(N-dimethylaminomethyleneaminomethyl)-1,2,4-oxadiazole

A mixture of 26 g of 5-aminomethyl-3-ethyl-1,2,4-oxadiazole and 30 ml of dimethylformamide dimethylacetal is heated for 6 1/2 hours to 80° C. (bath temperature). Subsequently, 16 ml of methanol is removed by distillation and the resultant product is purified by bulb tube distillation, thus obtaining 27.9 g (74.8%) of an oil having a boiling point of 130-150° C. (0.05 torr); $n_D^{20}$:1.4924.

(b)

1-Dimethylamino-3-(3-ethyl-1,2,4-oxadiazol-5-yl)-4-pyrrolidinyl)-2-azapenta-1,3-diene (E,Z Mixture)

13.6 g of the product obtained in (a), 15.0 g of dimethylacetamide dimethylacetal and 8.0 g of pyrrolidine are heated for 21 hours under nitrogen to 80° C. (bath temperature). The thus-formed alcohol is distilled off subsequently, and the reaction product is purified by bulb tube distillation, thus obtaining 15.4 g of a fraction that distills at 215°614 230° C. (0.04 torr). By recrystallization from n-hexane, 9.5 g (45.7%) of azadiene 5 is obtained with a melting point of 59°-62° C.

Azadiene 6

(a) Methoxyacetic Acid Dimethylamide Dimethylacetal

Under cooling, 42.2 g of methoxyacetic acid dimethylamide is added in three portions to 53.4 g of trimethyloxonium tetrafluoroborate. The reaction mixture is then stirred for 2 hours at room temperature and then allowed to stand overnight. After dissolution in 40 ml of dichloromethane, the thus-formed salt is gradually added to a solution of sodium methoxide in methanol (prepared by dissolving 10.4 g of sodium in 225 ml of methanol). Thereafter, the mixture is further stirred for 2 hours at room temperature. For working up purposes, the formed precipitate is suctioned off and rinsed with a small amount of ethanol. The filtrate forms 2 phases after the solvents have been removed by distillation. By bulb tube distillation, the top phase yields 21.8 g (36%) of the desired product with a boiling point of 54°-57° C. (14 torr); $n_D^{20}$:1.4204.

(b)

1-Dimethylamino-3-(3-ethyl-1,2,4-oxadiazol-5-yl)-5-methoxy-4-(1-pyrrolidinyl)-2-azapenta-1,3-diene (E,Z Mixture)

8.8 g of the product prepared in (a) is reacted with 6.6 g of 3-ethyl-5-(N-dimethylaminomethyleneaminomethyl)-1,2,4-oxadiazole and 4.5 ml of pyrrolidine analogously to the preparation of azadiene 5. By bulb tube distillation, 11.8 g (quant.) of azadiene 6 is obtained with a boiling point of 200-240° C. (0.05 torr).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, unless otherwise indicated, all parts and percentages are by weight.

The entire texts of all applications, patents and publications, if any, cited above and below, and of corresponding application P 37 42 716.4, are hereby incorporated by reference.

Example 1

(a)

4-(3-Ethyl-1,2,4-oxadiazol-5-yl)-1-(3-hydroxyphenyl)imidazole

A solution of 6.19 g of azadiene 2 in 20 ml of glacial acetic acid is combined under cooling with 2.18 g of 3-hydroxyaniline and then stirred for 16 hours under nitrogen at room temperature. Thereafter the mixture is heated for 1½ hours to 100° C. (bath temperature). For working up purposes, the reaction mixture is diluted under cooling with sodium bicarbonate solution, the thus-formed crystallized product is suctioned off, rinsed with water, and dried. Recrystallization from ethanol yields 4.77 g (93.2%)

of the title compound with a melting point of 214°-215° C.

The following compounds are obtained analogously to Example 1(a):

(b) 4-(3-ethyl-1,2,4-oxadiazol-5-yl)-1-(2-hydroxyphenyl)imidazole by reaction with 2-hydroxyaniline; mp 200°-202° C. (isopropanol), (c) 1-(2,6-dihydroxyphenyl)-4-(3-ethyl-1,2,4-oxadiazol-5-yl)imidazole by reaction with 2,6-dihydroxyaniline; mp 239°-240° C. (ethanol).

Example 2

1-(2,6-Dihydroxyphenyl)imidazole-4-carboxylic Acid Ethyl Ester

A solution of 2.8 g of azadiene 1 in 10 ml of glacial acetic acid is reacted with 1.25 g of 2,6-dihydroxyaniline in the way described in Example 1(a) After working up and recrystallization from acetonitrile, 1.9 g of the title compound is obtained, mp 229°-230° C.

Example 3

(a)

1-(2-Benzyloxyphenyl)-4-(3-ethyl-1,2,4-oxadiazol-5-yl)imidazole

A solution of 256 mg of the compound prepared in 1(b) in 2 ml of anhydrous dimethylformamide is combined with 83 mg of potassium carbonate and stirred for one hour at room temperature. Subsequently, 152 mg of benzyl chloride is added and the reaction mixture is stirred initially overnight at room temperature, then, to complete the reaction, for one hour at 80° C. (bath temperature). For working up, the reaction mixture is diluted with ether, the thus-formed precipitate is suctioned off and dried. Recrystallization from isopropanol yields 152 mg (43.9%) of the title compound with a melting point of 106° C.

The following compounds are obtained analogously:

(b) 1-[2-(4-Chlorobenzyloxy)phenyl]-4-(3-ethyl-1,2,4-oxadiazol-5-yl)imidazole by reaction of the compound prepared in Example 1(b) with 4-chlorobenzyl chloride; mp: 88°-89° C. (isopropanol).

(c) 1-[2-(2-Phenylethoxy)phenyl]-4-(3-ethyl-1,2,4-oxadiazol-5-yl)imidazole by reaction of the compound produced in Example 1(b) with 2-phenethyl bromide; mp:61°-61° C. (diisopropyl ether).

(d) 1-(2,6-Dibenzyloxyphenyl)-4-(3-ethyl-1,2,4-oxadiazol-5-yl)imidazole by reaction of the compound prepared in Example 1(c) with benzyl chloride; mp: 149°-150° C. (ethanol).

(e) 1-(2,6-Dibenzyloxyphenyl)imidazole-4-carboxylic Acid Ethyl Ester by reaction of the compound produced in Example 2 with benzyl chloride; mp: 125°-126° C. (isopropanol).

(f) 4-(3-Ethyl-1,2,4-oxadiazol-5-yl)-1-[3-(2-phenylethoxy)phenyl]imidazole by reacting the compound produced in Example 1(a) with 2-phenethyl bromide; mp: 124°-125° C. (diisopropyl ether/ethanol).

(g) 1-[3-(4-Chlorobenzyloxy)phenyl]-4-(3-ethyl-1,2,4-oxadiazol-5-yl)imidazole by reaction of the compound prepared in Example 1(a) with 4-chlorobenzyl chloride; mp: 137°-138° C. (acetonitrile).

Example 4

4-(3-Ethyl-1,2,4-oxadiazol-5-yl)-1-[3-(4-nitrophenoxy)phenyl]imidazole

A solution of 2.56 g of azadiene 2 in 40 ml of anhydrous dimethylformamide is combined with 976 mg of potassium carbonate and stirred for 15 minutes under nitrogen at 100° C. (bath temperature). After cooling to room temperature, 1.47 g of 4-fluoronitrobenzene is added and the mixture is agitated at 100° C. until complete reaction has occurred. After withdrawing the solvent, the residue is taken up in water, the thus-formed precipitate is suctioned off and rinsed with water. Recrystallization from ethanol yields 3.74 g (99.1%) of the title compound with a melting point of 145°-146° C.

Example 5

1-[3-(4-Aminophenoxy)phenyl]-4-(3-ethyl-1,2,4-oxadiazol-5-yl)imidazole 745 mg of the compound disclosed in Example 4 is hydrogenated in 80 ml of ethanol/tetrahydrofuran (1:1) in the presence of 3 g of Raney nickel under normal conditions. After hydrogen absorption has ceased, the catalyst is suctioned off, thoroughly rinsed, and the filtrate is concentrated. Chromatography of the crude product on silica gel with dichloromethane/methanol (95:5) and subsequent recrystallization from diisopropyl ether yield 357 mg (51.5%) of the title compound with a melting point of 131°-133° C.

Example 6

(a) 1-(4-Benzyloxyphenyl)-4-(3-ethyl-1,2,4-oxadiazol-5-yl)imidazole

A solution of 1.6 g of azadiene 2 in 5 ml of glacial acetic acid is reacted with 1.0 g of 4-benzyloxyaniline in the way described in Example 1(a). After the reaction mixture has been worked up and recrystallized from acetonitrile, 1.26 g (73%) of the title compound is obtained, mp 171°–172° C.

The following compounds are obtained analogously:

(b) 1-(3-Benzyloxyphenyl)-4-(3-ethyl-1,2,4-oxadiazol-5-yl)imidazole by reaction with 3-benzyloxyaniline; mp: 113°–114° C. (ethanol).

(c) 4-(3-Ethyl-1,2,4-oxadiazol-5-yl)-1-(3-phenoxyphenyl)imidazole by reaction with 3-phenoxyaniline; mp: 108°–109° C. (acetonitrile).

(d) 1-[3-(4-Chlorophenoxy)phenyl]-4-(3-ethyl-1,2,4-oxadiazol-5-yl)imidazole by reaction with 3-(4-chlorophenoxy)aniline; mp: 120°–122° C. (ethanol).

EXAMPLE 7

(a) 1-(5-Chloro-2-methoxyphenyl)-4-(3-ethyl-1,2,4-oxadiazol-5-yl)imidazole

A solution of 619 mg of azadiene 2 in 2 ml of glacial acetic acid is reacted with 315 mg of 5-chloro-2-methoxyaniline in the way disclosed in Example 1(a). After working up and recrystallization from ethanol, 362 mg (59.4% of the title compound is obtained with a melting point of 139°–140° C.

The following compounds are obtained analogously:

(b) 1-(2-Chloro-5-methoxyphenyl)-4-(3-ethyl-1,2,4-oxadiazol-5-yl)imidazole by reaction with 2-chloro-5-methoxyaniline; mp: 67°–69° C. (diisopropyl ether).

(c) 1-(2-Benzyloxy-5-chlorophenyl)-4-(3-ethyl-1,2,4-oxadiazol-5-yl)imidazole by reaction with 5-chloro-2-benzyloxyaniline; mp: 100°–102° C. (ethanol).

(d) 1-(3,4-Methylenedioxyphenyl)-4-(3-ethyl-1,2,4-oxadiazol-5-yl)imidazole by reacting with 3,4-methylenedioxyaniline; mp: 173°–174° C. (ethanol).

(e) 1-(3,4-Dimethoxyphenyl)-4-(3-ethyl-1,2,4-oxadiazol-5-yl)imidazole by reaction with 3,4-dimethoxyaniline; mp: 143° C. (ethanol).

(f) 1-(3,4-Dimethoxyphenyl)imidazole-4-carboxylic Acid Ethyl Ester by reacting azadiene 1 with 3,4-dimethoxyaniline; mp: 125°–126° C. (ethyl acetate).

Example 8

(a) 1-(3-Methoxyphenyl)imidazole-4-carboxylic Acid Ethyl Ester

A solution of 1.4 g of azadiene 1 in 5 ml of glacial acetic acid is combined with 0.6 ml of m-anisidine and stirred overnight at room temperature. For completing the reaction, the mixture is thereafter stirred for another hour at 100° C. (bath temperature). After the usual steps of working up and chromatography on silica gel with toluene/ethanol (97:3), 1.18 g (96%) of the title compound is obtained with a melting point of 95°–96° C. (toluene).

The following compounds are obtained analogously:

(b) 4-(3-Ethyl-1,2,4-oxadiazol-5-yl)-1-(3-methoxyphenyl)imidazole by reaction of azadiene 2 with m-anisidine; mp: 89°–90° C. (ethanol).

(c) 1-(3-Ethoxyphenyl)-4-(3-ethyl-1,2,4-oxadiazol-5-yl)imidazole by reaction of azadiene 2 with phenetidine; mp: 120°–121° C. (ethanol).

(d) 1-(4-Methoxyphenyl)imidazole-4-carboxylic Acid Ethyl Ester by reacting azadiene 1 with p-anisidine; mp: 93°–94° C. (toluene).

(e) 4-(3-Ethyl-1,2,4-oxadiazol-5-yl)-1-(4-methoxyphenyl)imidazole by reaction of azadiene 2 with p-anisidine; mp: 147°–148° C. (ethanol).

(f) 1-(4-Phenoxyphenyl)imidazole-4-carboxylic Acid Ethyl Ester by reaction of azadiene 1 with p-phenoxyaniline; mp: 113°–114° C. (toluene).

(g) 4-(3-Ethyl-1,2,4-oxadiazol-5-yl)-1-(4-phenoxyphenyl)imidazole by reacting azadiene 2 with p-phenoxyaniline; mp: 172°–173° C. (ethanol).

Example 9

1-(3-Methoxyphenyl)imidazole-4-carboxylic Acid Isopropyl Ester

A solution of 615 mg of the compound obtained in Example 8(a) and 0.8 ml of titanium isopropylate is heated under reflux for 8 hours under a protective gas. The reaction mixture is subsequently concentrated, the residue is taken up in ethyl acetate and extracted by shaking with a small amount of 2N HCl. Thereafter, the mixture is neutralized with sodium carbonate solution, extracted with ethyl acetate, dried over sodium sulfate, and concentrated. By chromatography of the residue on silica gel with hexane/acetone (7:3), 560 mg (86%) of the title compound is obtained as a slightly yellow oil.

Example 10

(a) 4-(3-Ethyl-1,2,4-oxadiazol-5-yl)-1-[3-(2-propenyl)oxyphenyl]imidazole

A solution of 513 mg of the compound prepared in Example 1(a) in 10 ml of anhydrous dimethylformamide is combined under nitrogen with 165 mg of potassium carbonate and heated for 15 minutes to 100° C. After cooling, 363 mg of allyl bromide is added and the mixture is again heated for 3½ hours to 100° C. Thereafter the solvent is distilled off, the residue is triturated with water, suctioned off, and thoroughly rinsed with water. After drying, the thus-obtained crude product is purified by chromatography on silica gel with toluene/ethyl acetate (8:2). After recrystallization from diisopropyl ether, 454 mg (76.6%) of the title compound is obtained with a melting point of 73°–74° C.

The following compounds are obtained analogously:

(b) 4-(3-Ethyl-1,2,4-oxadiazol-5-yl)-1-(3-isopropoxyphenyl)imidazole by reaction with isopropyl bromide, mp: 107° C. (ethanol/n-hexane).

(c) 1-(3-Cyclopentyloxyphenyl)-4-(3-ethyl-1,2,4-oxadiazol-5-yl)imidazole by reaction with cyclopentyl bromide; mp: 132° C. (diisopropyl ether).

(d) [3-(5-Bromo-2-pyridyloxy)phenyl]-4-(3-ethyl-1,2,4-oxadiazol-5-yl)imidazole by reaction with 2,5-dibromopyridine; mp: 141°–142° C. (ethanol).

Example 11

1-(3-Hydroxyphenyl)imidazole-4-carboxylic Acid Ethyl Ester 13.91 g of azadiene 1 and 5.46 g of 3-hydroxyaniline are reacted in 50 ml of glacial acetic acid in analogy to Example 1(a). After the reaction mixture has been worked up with sodium bicarbonate solution, the resultant crude product is recrystallized from ethyl acetate, obtaining in this way 11.17 g (96.2%) of the title compound with a melting point of 164°–165° C.

Example 12

(a)  1-(3-Isopropoxyphenyl)imidazole-4-carboxylic Acid Ethyl Ester

A mixture of 696 mg of the compound prepared in Example 11, 405 mg of isopropyl bromide and 248 mg of potassium carbonate in 15 ml of anhydrous dimethylformamide is heated under nitrogen for one hour to 100° C. With incomplete reaction, equivalent amounts of isopropyl bromide and potassium carbonate are furthermore added two to three times. For working up purposes, the solvent is distilled off and the remaining residue is stirred with water. The thus-obtained crude product is filtered off, dried, and purified by chromatography on silica gel with toluene/ethyl acetate (8:2), thus producing 782 mg (95%) of the title compound as a slightly yellow oil.

The following compounds are obtained analogously:

(b) 1-(3-Cyclopentyloxyphenyl)imidazole-4-carboxylic Acid Ethyl Ester by reaction with cyclopentyl bromide; mp: 66°–67° C. (cyclohexane).

(c) 1-[3-(2-Propenyloxy)phenyl]imidazole-4-carboxylic Acid Ethyl Ester by reacting with allyl bromide; mp: 53°–55° C. (diisopropyl ether).

(d) 1-[3(5-Bromo-2-pyridyloxy)phenyl]imidazole-4-carboxylic Acid Ethyl Ester by reaction with 2,5-dibromopyridine, mp: 103°–105° C. (diisopropyl ether).

(e) 1-[3-(4-Nitrophenoxy)phenyl]imidazole-4-carboxylic Acid Ethyl Ester by reacting with 4-fluoronitrobenzene; mp: 162°–163° C. (ethanol).

Example 13

1-[3-(4-Aminophenoxy)phenyl]imidazole-4-carboxylic Acid Ethyl Ester 2.83 g of the compound prepared in Example 12(e) is hydrogenated in 320 ml of ethanol/tetrahydrofuran (2:1) in the presence of 12 g of Raney nickel under normal conditions. After hydrogen absorption is complete, the catalyst is filtered off and thoroughly washed out with ethanol. The filtrate yields, by concentrating and recrystallizing from ethanol, 1.52 g (58.9%) of the title compound with a melting point of 162°–163° C.

Example 14

1-[3-(4-Chlorophenoxy)phenyl]imidazole-4-carboxylic Acid Ethyl Ester 1.3 g of the compound produced in Example 13 is dissolved at −5° C. in 30 ml of concentrated HCl/water (1:1) and combined dropwise with a solution of 286 mg of sodium nitrite in 4 ml of water. After stirring for another 50 minutes, the reaction mixture is gradually added to a cooled solution of 455 mg of copper(I) chloride in 6.7 ml of concentrated HCl. The mixture is further stirred for 15 minutes at −5° to 0° C. Subsequently, the mixture is gradually warmed to room temperature (about 30 minutes), then stirred for another 30 minutes at 85° C. After cooling, the mixture is diluted with water and the thus-formed precipitate is suctioned off. This precipitate is then extracted by shaking between ethyl acetate and a 12% strength ammonia solution. The aqueous phase is repeatedly extracted thoroughly with dichloromethane. Subsequently, the combined organic phases are washed with saturated sodium chloride solution and water, dried over sodium sulfate, and concentrated. From the crude product, by chromatography on silica gel with a toluene/ethyl acetate gradient, 312 mg (22.7%) of the title compound is obtained with a melting point of 112°–113° C. (ethanol).

Example 15

1-(3-Cyclopentyloxyphenyl)imidazole-4-carboxylic Acid Isopropyl Ester 480 mg of the compound prepared in Example 12(b) is reacted in 20 ml of anhydrous isopropanol analogously to Example 9 with 277 mg of titanium isopropylate. After working up and chromatography on silica gel with hexane/acetone (8:2), 403 mg (80.1%) of the title compound is obtained as a slightly yellow oil.

Example 16

1-(3-Benzyloxyphenyl)imidazole-4-carbonitrile

A solution of 1.8 g of azadiene 3 in 10 ml of glacial acetic acid is combined with 2 g of 3-benzyloxyaniline and stirred overnight at room temperature. Then the reaction mixture is heated for one hour to 100° C. After the usual working up step and chromatography on silica gel with toluene/ethyl acetate (9:1), 2.4 g (86%) of the title compound is obtained as a slightly yellow oil.

Example 17

(a) 1-(3-Hydroxyphenyl)-5-methylimidazole-4-carbonitrile

A solution of 24.8 g of azadiene 4 in 100 ml of glacial acetic acid is combined with 10.9 g of 3-hydroxyaniline and stirred for two days at room temperature, After the reaction mixture has subsequently been heated for five hours to 100° C., it is concentrated, the residue taken up in ethyl acetate and neutralized with potassium carbonate solution. The crude product remaining after concentration of the ethyl acetate phase is purified by chromatography on silica gel with dichloromethane/methanol (95:5) and subsequent recrystallization from acetonitrile, yielding 6.64 g (33%) of the title compound with a melting point of 205°–207° C.

(b) 1-(3-Hydroxyphenyl)-5-methylimidazole-4-formamidoxime

A solution of 6.37 g of the compound described in 17(a) in 250 ml of anhydrous ethanol is combined with 3.3 g of hydroxylammonium chloride and 6.6 g of potassium carbonate and refluxed for three hours. After complete reaction, the solvent is distilled off and the residue extracted by shaking between water and ethyl acetate. After drying over sodium sulfate and concentration, 6.6 g (88.9%) of the title compound is obtained from the ethyl acetate phase; this product is further used without additional purification.

(c) 4-(5-Ethyl-1,2,4-oxadiazol-3-yl)-1-(3-hydroxyphenyl)-5-methylimidazole 6.6 g of the crude product described in 17(b) is dissolved in 500 ml of anhydrous tetrahydrofuran and gradually combined with 3.3 ml of propionyl chloride. The reaction mixture is then stirred overnight at room temperature. Thereafter the solvent is distilled off, the residue is combined with xylene and refluxed for 3½ hours. After concentrating, the crude product is purified by chromatography on silica gel with dichloromethane/methanol (95:5), thus obtaining 5.8 g (75%) of the title compound with a melting point of 226°–227° C. (acetonitrile).

(d) 1-(3-Cyclopentyloxyphenyl)-4-(5-ethyl-1,2,4-oxadiazol-3-yl)-5-methylimidazole A mixture of 1.8 g of the compound prepared in 17(c), 730 mg of cyclopentyl chloride and 550 mg of potassium carbonate is heated in 30 ml of anhydrous dimethylformamide for one hour under nitrogen to 100° C. For working up purposes, the solvent is distilled off and the residue stirred together with water. The thus-formed crude product is dried and purified by chromatography on silica gel with toluene/ethyl acetate (8:2), thus producing 1.63 g (73%) of the title compound as a slightly yellow oil.

Example 18

(a) 5-Methyl-1-(3-phenoxyphenyl)imidazole-4-carbonitrile

A solution of 7.4 g of azadiene 4 in 30 ml of glacial acetic acid is combined with 7.7 g of 3-phenoxyaniline and stirred for four days at room temperature. Thereafter the reaction mixture is heated for four hours to 100° C. For working up purposes, the mixture is neutralized with potassium carbonate solution and extracted with ethyl acetate. The ethyl acetate phase is washed with water, dried over sodium sulfate and concentrated. The resultant crude product is purified by chromatography on silica gel with dichloromethane/methanol (9:1). After recrystallization from methyl tert-butyl ether, 2.44 g of the title compound is obtained with a melting point of 97°–98° C.

(b) 5-Methyl-1-(3-phenoxyphenyl)imidazole-4-formamidoxime 2.2 g of the compound described in 18(a) is dissolved in 80 ml of anhydrous ethanol and combined with 1.67 g of hydroxylammonium chloride and 1.66 g of potassium carbonate. The reaction mixture is then refluxed for two hours. For working up of the mixture, the solvent is distilled off and the residue stirred together with water. The thus-formed crystals are suctioned off, dried and recrystallized from ethanol, thus obtaining 1.33 g (54%) of the title compound with a melting point of 196°–198° C.

(c) 4-(5-Ethyl-1,2,4-oxadiazol-3-yl)-5-methyl-1-(3-phenoxyphenyl)imidazole

A solution of 1.23 g of the compound disclosed in 18(b) in 100 ml of anhydrous tetrahydrofuran is combined with 0.47 ml of propionyl chloride and stirred for 16 hours at room temperature. After concentration, the residue is taken up in 40 ml of xylene and refluxed for three hours. For working up purposes, the solvent is distilled off and the remaining crude product is extracted by shaking between potassium carbonate solution and ethyl acetate. From the ethyl acetate phase, after washing with water and drying over sodium sulfate, 1.15 g (83%) of the title compound is obtained as a slightly yellow oil.

Example 19

1-(3-Benzyloxyphenyl)-4-(3-ethyl-1,2,4-oxadiazol-5-yl)-5-methylimidazole

A solution of 1 g of azadiene 5 in 5 ml of glacial acetic acid is combined with 0.58 g of 3-benzyloxyaniline and stirred for 16 hours at room temperature. Subsequently the reaction mixture is heated for one hour to 100° C. After working up and chromatography on silica gel with toluene/ethanol (9:1), 682 mg (65%) of the title compound is obtained as a slightly yellow oil.

Example 20

(a) 4-(3-Ethyl-1,2,4-oxadiazol-5-yl)-1-(3-hydroxyphenyl)-5-methoxymethylimidazole A solution of 15.4 g of azadiene 6 in 42 ml of glacial acetic acid is combined with 4.55 g of 3-hydroxyaniline and stirred for three days at room temperature under nitrogen. Subsequently, the mixture is heated for another two hours to 100° C. For working up purposes, the reaction mixture is diluted with water, rendered alkaline with potassium carbonate solution, and extracted with ethyl acetate. The ethyl acetate phase is washed in succession with potassium carbonate solution, sodium chloride solution and water, dried over sodium sulfate, and concentrated. Chromatography on silica gel with a toluene/ethyl acetate gradient yields, from the crude product, 9.24 g (73.8%) of the title compound with a melting point of 98°–99° C. (methyl tert-butyl ether).

Analogously, the following compounds are obtained:

(b) 4-(3-Ethyl-1,2,4-oxadiazol-5-yl)-5-methoxymethyl-1-(3-methoxyphenyl)imidazole by reaction with 3-methoxyaniline; mp: 66°–68° C. (n-hexane).

(c) 1-[3-(4-Chlorophenoxy)phenyl]-4-(3-ethyl-1,2,4-oxadiazol-5-yl)-5-methoxymethylimidazole by reaction with 3-(4-chlorophenoxy)aniline; mp: 68°–70° C. (cyclohexane/n-hexane).

(d) 1-(3-Benzyloxyphenyl)-4-(3-ethyl-1,2,4-oxadiazol-5-yl)-5-methoxymethylimidazole by reaction with 3-benzyloxyaniline; mp: 63°–64° C. (n-hexane).

Example 21

(a) 1-(3-Cyclopentyloxyphenyl)-4-(3-ethyl-1,2,4-oxadiazol-5-yl)-5-methoxymethylimidazole A solution of 901 mg of the compound described in Example 20(a) in 15 ml of anhydrous dimethylformamide is combined with 980 mg of cyclopentyl bromide and 500 mg of potassium carbonate and heated for six hours to 100° C. For working up purposes the solvent is distilled off, the residue is combined with water and extracted with ethyl acetate. The ethyl acetate phase is washed with water, dried over sodium sulfate, and concentrated. Chromatography on silica gel with toluene/ethyl acetate (9:1) yields 1.07 g (96.8%) of the title compound as a slightly yellow oil.

The following compounds are obtained analogously:

(b) 4-(3-Ethyl-1,2,4-oxadiazol-5-yl)-5-methoxymethyl-1-[3-(4-nitrophenoxy)phenyl]imidazole by reaction with 4-fluoronitrobenzene; mp: 126°–127° C. (acetonitrile).

(c) 1-[3-(4-Chlorobenzyloxy)phenyl]-4-(3-ethyl-1,2,4-oxadiazol-5-yl)-5-methoxymethylimidazole by reaction with 4-chlorobenzyl chloride; slightly yellow oil.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of this invention to adapt it to various usages and conditions.

What is claimed is:

1. An imidazole compound of the formula

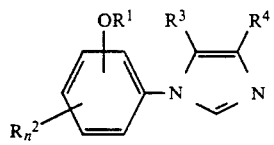

wherein
R$^1$ is hydrogen; C$_{1-10}$-alkyl substituted by halogen, hydroxy, C$_{1-4}$-alkoxy, amino, C$_{1-4}$-alkylamino or C$_{1-4}$-dialkylamino; C$_{1-10}$-perfluoroalkyl; C$_{2-10}$-alkenyl; C$_{2-10}$-alkenyl substituted as indicated for alkyl; C$_{2-10}$-alkynyl; C$_{2-10}$-alkynyl substituted as indicated for alkyl; C$_{3-10}$-cycloalkyl; C$_{3-10}$-cycloalkyl substituted as indicated for alkyl; C$_{3-10}$-cycloalkenyl; C$_{3-10}$-cycloalkenyl substituted as indicated for alkyl; C$_{3-10}$-cycloalkyl or cycloalkenyl wherein a —CH$_2$— group is replaced by an oxygen atom; C$_{6-10}$-aryl; C$_{6-10}$-aryl substituted by 1-3 of halogen, nitro, cyano, hydroxy, mercapto, C$_{1-4}$-alkyl, C$_{1-4}$-alkoxy, C$_{1-4}$-alkylthio, C$_{1-4}$-alkylsulfinyl, C$_{1-4}$-alkylsulfonyl, or amino mono- or disubstituted by C$_{1-4}$-alkyl, C$_{1-4}$-alkanoyl or sulfonyl; C$_{7-10}$-aralkyl; C$_{7-10}$-aralkyl mono- or disubstituted in the aryl portion by halogen, C$_{1-4}$-alkoxy, C$_{1-4}$-alkyl, or amino mono- or disubstituted by C$_{1-4}$-alkyl, C$_{1-4}$-alkanoyl or sulfonyl; C$_{5-6}$-heteroaryl containing one or two sulfur, oxygen or nitrogen atoms; C$_{5-6}$-heteroaryl containing one or two sulfur, oxygen or nitrogen atoms substituted on a carbon atom as defined for aryl;

n is 1-2;

R$^2$ is hydrogen halogen, amino, mono- or disubstituted amino, azide, thiocyanate or cyano, C$_{1-10}$-alkyl, C$_{1-10}$-alkyl substituted by halogen, or an —OR$^1$ group wherein R$^1$ is selected from the groups defined above, or when OR$^1$ and R$^2$ are on adjacent C-atoms, then
R$^1$ and R$^2$ jointly with the oxygen atom can form a saturated or unsaturated 5- to 7-membered ring, or such a ring which contains a nitrogen, sulfur or additional oxygen atom, R$^3$ is hydrogen, C$_{1-6}$-alkyl, or C$_{1-6}$-alkoxyalkyl, R$^4$ is —COOR$^5$, —CONR$^6$R$^7$, —CN,

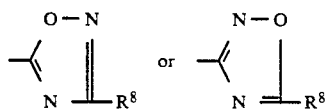

wherein
R$^5$ is hydrogen, C$_{1-6}$-alkyl,
R$^6$ and R$^7$ are each independently C$_{1-7}$-alkyl, C$_{3-7}$-cycloalkyl, C$_{3-7}$-cycloalkenyl, or jointly with the nitrogen atom R$^6$ and R$^7$ form a saturated five-or six-membered ring, or such a ring that contains an oxygen, sulfur or an additional nitrogen atom, R$^8$ is hydrogen, C$_{1-7}$-alkyl, C$_{3-7}$-cycloalkyl or C$_{3-7}$-cycloalkenyl.

2. An imidazole derivative according to claim 1 wherein R$^4$ is COOR$^5$,

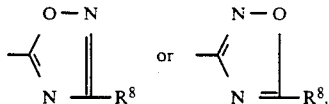

3. A compound according to claim 1, wherein R$^1$ is C$_{1-6}$-alkyl, C$_{1-6}$-alkenyl, C$_{3-7}$-cycloalkyl or C$_{3-7}$-cycloalkylalkyl.

4. A compound according to claim 1, wherein R$^1$ is 1-propenyl, 2-propenyl, 3-methyl-2-propenyl or 2-propynyl.

5. A compound according to claim 1, wherein R$^1$ is C$_{1-10}$-perfluoroalkyl.

6. A compound according to claim 1, wherein R$^1$ is cyclopropylmethyl, cyclopropylethyl or cyclopentylmethyl.

7. A compound according to claim 1, wherein R$^1$ is 3-tetrahydrofuranyl or 3-tetrahydropyranyl.

8. A compound according to claim 1, wherein R$^1$ is 2,4-dichlorophenyl, 2-cyanophenyl, 4-aminophenyl, benzyl, phenethyl, α-methylbenzyl, 4-chlorophenethyl or 3-bromobenzyl.

9. A compound according to claim 1, wherein R$^1$ is pyridine, pyrimidine, pyrazine, pyridazine, furan, thiophene, pyrrole, imidazole, thiazole or 5-bromopyridine.

10. A compound according to claim 1, wherein R$^6$ and R$^7$ together are pyrrolidine, piperidine, morpholine, piperazine, thiomorpholine, 2,6-dimethylmorpholine or N-methylpiperazine.

11. 4-(3-Ethyl-1,2,4-oxadiazol-5-yl)-1-(2-hydroxyphenyl)imidazole,
  1-(2-benzyloxyphenyl)-4-(3-ethyl-1,2,4-oxadiazol-5-yl)imidazole,
  1-[2-(4-chlorobenzyloxy)phenyl]-4-(3-ethyl-1,2,4-oxadiazol-5-yl)imidazole,
  1-[2-(2-phenylethoxy)phenyl]-4-(3-ethyl-1,2,4-oxadiazol-5-yl)imidazole,
  4-(3-ethyl-1,2,4-oxadiazol-5-yl)-1-(3-hydroxyphenyl)imidazole,
  1-(3-benzyloxyphenyl)-4-(3-ethyl-1,2,4-oxadiazol-5-yl)imidazole,
  1-[3-(4-chlorobenzyloxy)phenyl]-4-(3-ethyl-1,2,4-oxadiazol-5-yl)imidazole,
  4-(3-ethyl-1,2,4-oxadiazol-5-yl)-1-[3-(2-phenylethoxy)phenyl]imidazole,
  4-(3-ethyl-1,2,4-oxadiazol-5-yl)-1-[3-(4-nitrophenoxy)phenyl]imidazole,
  1-[3-(4-aminophenoxy)phenyl]-4-(3-ethyl-1,2,4-oxadiazol-5-yl)imidazole,
  1-(4-benzyloxyphenyl)-4-(3-ethyl-1,2,4-oxadiazol-5-yl)imidazole,
  4-(3-ethyl-1,2,4-oxadiazol-5-yl)-1-(3-phenoxyphenyl)imidazole,
  1-[3-(4-chlorophenoxy)phenyl]-4-(3-ethyl-1,2,4-oxadiazol-5-yl)imidazole,
  1-(5-chloro-2-methoxyphenyl)-4-(3-ethyl-1,2,4-oxadiazol-5-yl)imidazole,
  1-(2-benzyloxy-2-chlorophenyl)-4-(3-ethyl-1,2,4-oxadiazol-5-yl)imidazole, 1-(2-chloro-5-methoxyphenyl)-4-(3-ethyl-1,2,4-oxadiazol-5-yl)imidazole,
1-(3,4-methylenedioxyphenyl)-4-(3-ethyl-1,2,4-oxadiazol-5-yl)imidazole,
1-(3,4-dimethoxyphenyl)imidazole-4-carboxylic acid ethyl ester,
1-(3,4-dimethoxyphenyl)-4-(3-ethyl-1,2,4-oxadiazol-5-yl)imidazole,
1-(2,6-dihydroxyphenyl)-4-(3-ethyl-1,2,4-oxadiazol-5-yl)imidazole,
1-(2,6-dihydroxyphenyl)imidazole-4-carboxylic acid ethyl ester,
1-(2,6-dibenzyloxyphenyl)imidazole-4-carboxylic acid ethyl ester,
1-(2,6-dibenzyloxyphenyl)-4-(3-ethyl-1,2,4-oxadiazol-5-yl)imidazole,
1-(3-methoxyphenyl)imidazole-4-carboxylic acid ethyl ester,
4-(3-ethyl-1,2,4-oxadiazol-5-yl)-1-(3-methoxyphenyl)imidazole,
1-(3-ethoxyphenyl)-4-(3-ethyl-1,2,4-oxadiazol-5-yl)imidazole,
1-(4-methoxyphenyl)imidazole-4-carboxylic acid ethyl ester,
4-(3-ethyl-1,2,4-oxadiazol-5-yl)-1-(4-methoxyphenyl)imidazole,
1-(4-phenoxyphenyl)imidazole-4-carboxylic acid ethyl ester,
4-(3-ethyl-1,2,4-oxadiazol-5-yl)-1-(4-phenoxyphenyl)imidazole,
1-(3-methoxyphenyl)imidazole-4-carboxylic acid isopropyl ester,
4-(3-ethyl-1,2,4-oxadiazol-5-yl)-1-[3-(2-propenyl)oxyphenyl]imidazole,
4-(3-ethyl-1,2,4-oxadiazol-5-yl)-1-(3-isopropoxyphenyl)imidazole,
1-(3-cyclopentyloxyphenyl)-4-(3-ethyl-1,2,4-oxadiazol-5-yl)imidazole,
[3-(5-bromo-2-pyridyloxy)phenyl]-4-(3-ethyl-1,2,4-oxadiazol-5-yl)imidazole,
1-(3-hydroxyphenyl)-imidazole-4-carboxylic acid ethyl ester,
1-(3-isopropoxyphenyl)imidazole-4-carboxylic acid ethyl ester,
1-(3-cyclopentyloxyphenyl)imidazole-4-carboxylic acid ethyl ester,
1-[3-(2-propenyloxy)phenyl]imidazole-4-carboxylic acid ethyl ester,
1-[3-[5-bromo-2-pyridyloxy)phenyl]imidazole-4-carboxylic acid ethyl ester,
1-[3-(4-nitrophenoxy)phenyl]imidazole-4-carboxylic acid ethyl ester,
1-[3-(4-aminophenoxy)phenyl]imidazole-4-carboxylic acid ethyl ester,
1-[3-(4-chlorophenoxy)phenyl]imidazole-4-carboxylic acid ethyl ester,
1-(3-cyclopentyloxyphenyl)imidazole-4-carboxylic acid isopropyl ester,
1-(3-benzyloxyphenyl)imidazole-4-carbonitrile,
1-(3-hydroxyphenyl)-5-methylimidazole-4-carbonitrile,
4-(5-ethyl-1,2,4-oxadiazol-3-yl)-1-(3-hydroxyphenyl)-5-methylimidazole,
1-(3-cyclopentyloxyphenyl)-4-(5-ethyl-1,2,4-oxadiazol-3-yl)-5-methylimidazole,
5-methyl-1-(3-phenoxyphenyl)imidazole-4-carbonitrile,
4-(5-ethyl-1,2,4-oxadiazol-3-yl)-5-methyl-1-(3-phenoxyphenyl)imidazole,
1-(3-benzyloxyphenyl)-4-(3-ethyl-1,2,4-oxadiazol-5-yl)-5-methylimidazole,
4-(3-ethyl-1,2,4-oxadiazol-5-yl)-1-(3-hydroxyphenyl)-5-methoxymethylimidazole,
4-(3-ethyl-1,2,4-oxadiazol-5-yl)-5-methoxymethyl-1-(3-methoxyphenyl)imidazole,
1-[3-(4-chlorophenoxy)phenyl]-4-(3-ethyl-1,2,4-oxadiazol-5-yl)-5-methoxymethylimidazole,
1-(3-benzyloxyphenyl)-4-(3-ethyl-1,2,4-oxadiazol-5-yl)-5-methoxymethylimidazole,
1-(3-cyclopentyloxyphenyl)-4-(3-ethyl-1,2,4-oxadiazol-5-yl)-5-methoxymethylimidazole,
4-(3-ethyl-1,2,4-oxadiazol-5-yl)-5-methoxymethyl-1-[3-(4-nitrophenoxy)phenyl]imidazole,
1-[3-(4-chlorobenzyloxy)phenyl]-4(3-ethyl-1,2,4-oxadiazol-5-yl)-5-methoxymethylimidazole, each a compound of claim 1.

12. A method for achieving an anxiolytic effect in a host, comprising administering to said mammalian host an effective amount of a compound of claim 1.

13. A pharmaceutical composition comprising a compound of claim 1 and a pharmaceutically acceptable carrier.

* * * * *